(12) United States Patent  (10) Patent No.: US 8,251,254 B2
Guggenmos et al. (45) Date of Patent: Aug. 28, 2012

(54) DEVICE AND SYSTEM FOR HANDLING OF DENTAL WORKPIECES

(75) Inventors: Sebastian Guggenmos, Peissenberg (DE); Michael Knee, Peissenberg (DE)

(73) Assignee: 3M Innovatives Properties Company, Saint Paul, MN (US)

( * ) Notice: Subject to any disclaimer, the term of this patent is extended or adjusted under 35 U.S.C. 154(b) by 303 days.

(21) Appl. No.: 12/671,521

(22) PCT Filed: Jul. 25, 2008

(86) PCT No.: PCT/US2008/071180
§ 371 (c)(1),
(2), (4) Date: Feb. 1, 2010

(87) PCT Pub. No.: WO2009/018146
PCT Pub. Date: Feb. 5, 2009

(65) Prior Publication Data
US 2011/0253734 A1    Oct. 20, 2011

(30) Foreign Application Priority Data
Aug. 2, 2007 (GB) .................................. 0714952.9

(51) Int. Cl.
*B65H 3/00* (2006.01)
(52) U.S. Cl. ........ 221/270; 221/251; 221/263; 221/264; 221/269; 221/272
(58) Field of Classification Search .................. 221/268, 221/269, 270, 272, 263, 264, 251
See application file for complete search history.

(56) References Cited

U.S. PATENT DOCUMENTS

| 1,796,470 | A | | 3/1931 | Meyer |
| 1,899,718 | A | | 2/1933 | Poston |
| 2,355,853 | A | | 8/1944 | Foxon |
| 2,409,783 | A | | 10/1946 | Moskey |
| 3,276,122 | A | | 10/1966 | Slayton |
| 3,313,452 | A | * | 4/1967 | Katz ............................. 221/268 |
| 4,068,767 | A | | 1/1978 | Tippetts |
| 4,178,121 | A | * | 12/1979 | Taylor .......................... 221/268 |
| 4,770,588 | A | * | 9/1988 | Ripatonda .................... 221/242 |
| 5,246,138 | A | * | 9/1993 | Blevins, Jr. .................. 221/263 |
| 5,383,752 | A | | 1/1995 | Rheinberger |
| 5,490,810 | A | | 2/1996 | Hahn |
| 5,615,505 | A | | 4/1997 | Vaid |

(Continued)

FOREIGN PATENT DOCUMENTS
EP    455854    11/1991
(Continued)

OTHER PUBLICATIONS
European Search Report 99 11 6985, 2 pgs.
(Continued)

*Primary Examiner* — Timothy Waggoner
(74) *Attorney, Agent, or Firm* — Pamela L. Stewart

(57) ABSTRACT

A device for handling workpieces. The device has a magazine (12) for holding at least one workpiece, and a delivery location (10). The device is retainable in the magazine by a retainer (s) (43) in the delivery location and displaceable to a position in which the workpiece because of its shape releases the retainer (s) so that the workpiece is free for being removed from the magazine. The device may provide for easy handling of workpieces and may be manufactured cost effectively.

35 Claims, 7 Drawing Sheets

U.S. PATENT DOCUMENTS

| | | | |
|---|---|---|---|
| 5,939,211 | A | 8/1999 | Mörmann |
| 6,224,371 | B1 | 5/2001 | De Luca |
| 6,454,568 | B1 * | 9/2002 | Beuschel et al. ............. 433/163 |
| 6,651,841 | B2 * | 11/2003 | Tsuchida ....................... 221/270 |
| 6,769,912 | B2 | 8/2004 | Beuschel |
| 7,431,545 | B2 | 10/2008 | Suttor |
| 2004/0020092 | A1 | 2/2004 | Christensen |
| 2005/0019121 | A1 | 1/2005 | Suttor |

FOREIGN PATENT DOCUMENTS

| | | |
|---|---|---|
| EP | 0807422 | 11/1997 |
| EP | 1658825 | 5/2006 |
| GB | 1394434 | 5/1975 |
| GB | 2123733 | 2/1984 |
| JP | 57048454 | 3/1982 |
| JP | 2000061835 | 2/2000 |
| JP | 2000070289 | 3/2000 |
| WO | WO 95/30382 | 11/1995 |
| WO | WO 03/041606 | 5/2003 |

OTHER PUBLICATIONS

International Search Report for PCT/US2008/071180, 7 pgs.
UK Search Report Application No. GB0714952.9, 3 pgs.
Written Opinion of the ISA for International Application No. PCT/US2008/071180, 9 pgs.

* cited by examiner

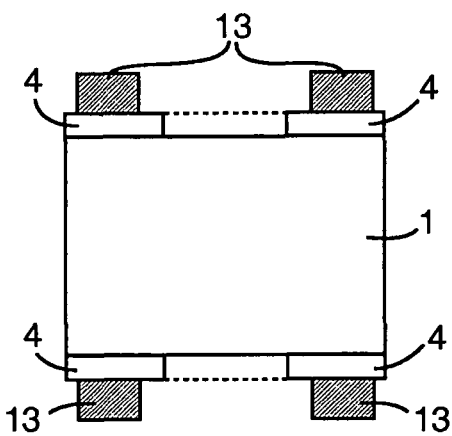
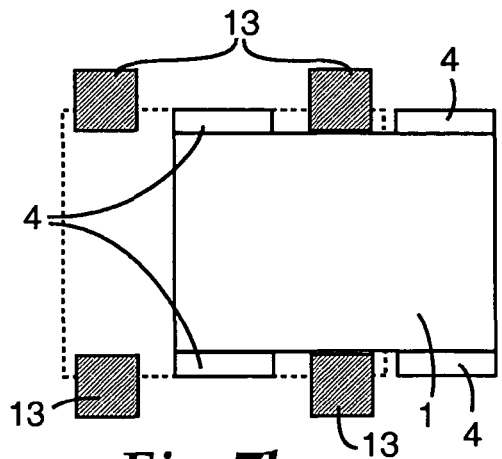
*Fig. 7a*  *Fig. 7b*
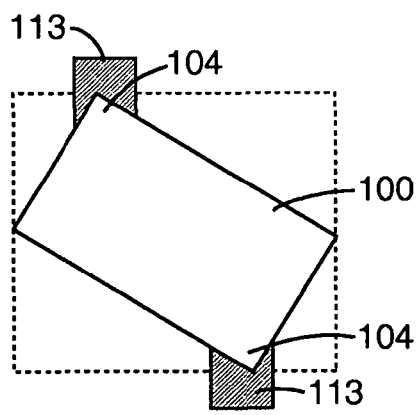
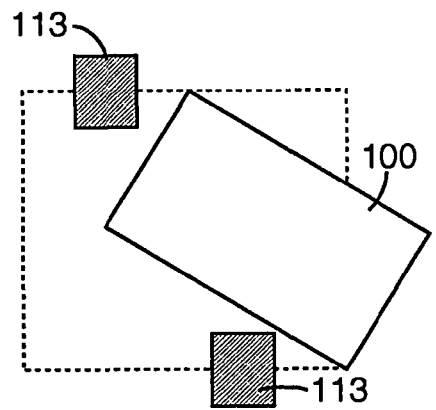
*Fig. 8a*  *Fig. 8b*
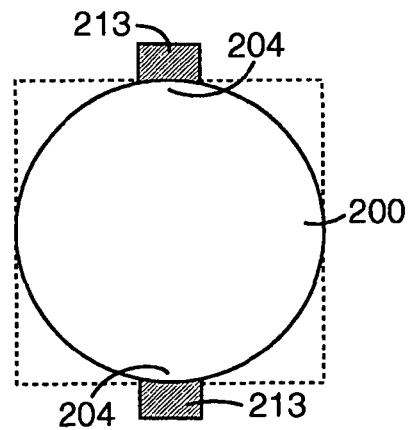
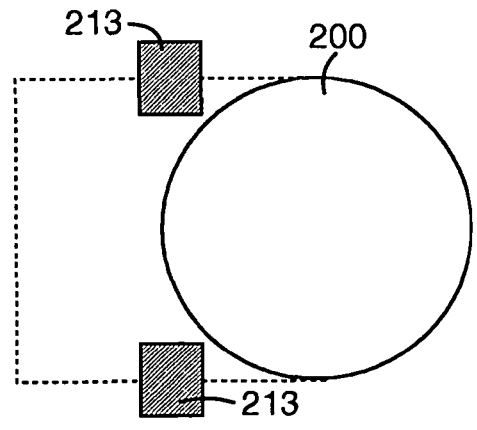
*Fig. 9a*  *Fig. 9b*

DEVICE AND SYSTEM FOR HANDLING OF DENTAL WORKPIECES

CROSS REFERENCE TO RELATED APPLICATIONS

This application is a national stage filing under 35 U.S.C. §371 of PCT/US2008/071180, filed Jul. 25, 2008, which claims priority to GB Application No. 0714952.9, filed Aug. 2, 2007, the disclosure of which is incorporated by reference in its/their entirety herein.

FIELD OF THE INVENTION

The invention relates to a device for handling of workpieces, in particular to a device allowing one or more workpieces to be stored in a magazine from which an individual workpiece can be removed, or into which the workpiece may be replaced, or both. The invention also concerns a system of a device and a workpiece and a method of handling workpieces.

BACKGROUND OF THE INVENTION

In recent years the manufacture of dental restorations or prostheses by use of automated processes has increased. Ceramic materials are often used in such automated processes which also allow for making high-quality dental restorations because of their good physical, aesthetic and biological properties. The manufacture of such restorations typically includes:
- capturing data representing the shape of a patient's teeth, for example by scanning a plaster model of the patient's teeth or alternatively by scanning the actual teeth in the patient's mouth;
- designing the shape of a frame based on the captured data using software, such as computer-aided design (CAD) software; and
- manufacturing the frame to correspond to the designed shape, for example, by an automated Computer Numerical Controlled (CNC) machine.

An exemplary CNC machine for making dental restorations is available from 3M ESPE AG (Seefeld, Germany) under the trade designation LAVA™ Milling Unit.

Machines of this type are designed to automatically machine a dental restoration or parts of a dental restoration. To permit continuous use, some of these machines are equipped with an input buffer holding blank material that is automatically fed into the machine for sequentially producing multiple dental restorations without the need of intervention. Accordingly such machines typically also have an output buffer that receives finished dental restorations.

Automated handling of multiple dental restorations, however, requires the control of materials and the data related to the manufacture of the dental restorations, especially because dental restorations typically are unique and associated with a patient whose tooth or teeth are intended to be restored. For this reason, in a process of manufacturing reliable tracking of each individual dental restoration is required. Furthermore it is required to handle blank materials as well as the prepared dental restorations with sufficient care to avoid damages for example chipping or cracking.

Although the current approaches for handling of material blanks and dental restorations may provide a variety of advantages, there is still a desire for an automated manufacturing device and process that are relatively inexpensive and work reliably.

SUMMARY OF THE INVENTION

A first aspect of the invention relates to a device for handling workpieces. The device comprises:
- a magazine for holding at least one workpiece,
- the magazine has a guiding section for guiding a workpiece in a feed direction toward a delivery location of the magazine, in the delivery location the workpiece is displaceable in a transfer direction between a first position and a second position,
- the magazine comprises at least one retainer at the delivery location,
- wherein in the first position the retainer(s) engage(s) the workpiece and restrain(s) the workpiece in the feed direction, and
- in the second position the workpiece is enabled to bypass the retainer(s) in the feed direction.

In the first position the retainer(s) may engage the workpiece and hinder the workpiece from being removed from the magazine in the feed direction, and in the second position the workpiece may be enabled to bypass the retainer(s) which allows the workpiece to be removed from the magazine in the feed direction.

The feed direction preferably corresponds to a direction which points from the guiding section toward the delivery location.

Preferably in the delivery location of the magazine the workpiece is displaceable in a transfer direction and relative to the retainer(s).

Removing the workpiece from the magazine preferably means moving the workpiece in the feed direction from the delivery location of the magazine to an outside location of the magazine. The workpiece may further be moved from the outside location of the magazine in the delivery location of the magazine opposite the feed direction for replacing the workpiece in a magazine. In this case the workpiece is preferably positioned to bypass the retainer(s) and to arrive in the delivery location in the second position, and thereafter to be moved to a first position.

In an embodiment of the invention the device for handling workpieces may comprise:
- A magazine for holding at least one workpiece.
- The magazine may have a guiding section and a delivery location.
- The guiding section is preferably adapted for guiding a workpiece along a feed direction into a first position in the delivery location.
- The magazine preferably comprises a retainer(s) at the delivery location that is/are configured to retain the workpiece in the magazine by engaging the workpiece in the first position, and wherein
- in delivery location the workpiece is displaceable in a transfer direction toward a second position in which recesses of the workpiece release the retainers so that the workpiece is free, for example to be moved, in the feed direction.

The device according to the invention is adapted such that when the workpiece is located in the first position in the delivery location the retainer(s) engage(s) the workpiece at a protrusion(s) and hinder(s) the workpiece from being removed from the magazine in the feed direction.

In the first position the retainer(s) may also engage the workpiece or protrusion(s) and prevent the workpiece from being removed from the magazine in the feed direction.

Preferably the magazine is oriented generally vertically. Thus, the workpieces drop or move toward the delivery location with the aid of gravity. Further, the feed direction is preferably a generally vertical direction. The guiding section and the delivery location are preferably arranged adjacent one another. In a preferred embodiment the delivery location is arranged at or adjacent an end of the magazine. Furthermore, the guiding section is preferably vertically arranged above the delivery location. The workpieces could, however, also be guided along another path.

Preferably the transfer direction is substantially transverse, and more preferably generally perpendicular, to the feed direction. For example, the transfer direction may be a horizontal direction when the feed direction is vertical. The distance between the first position and the second position is preferably less than the length of the workpiece in the transfer direction. In particular the distance between the first position and the second position may be less than 50% of the length of the workpiece in the transfer direction.

In one embodiment, in the guiding section the workpiece is movable in the feed direction and opposite to the feed direction, but displacement of the workpiece in the transfer direction is restricted. The guiding section may further be adapted to restrict a displacement of the workpiece in other directions transverse to the feed direction. The guiding section thus may be adapted to guide the workpiece into the delivery location in the first position. A workpiece inserted into the magazine may therefore be guided so that it arrives in the first position of the delivery location.

In another embodiment the delivery location is configured to allow the displacement of the workpiece in the transfer direction. For example, the guiding section may have or form a mechanical guideway for restricting the displacement of the workpiece in the transfer direction which is not present in the delivery location. The guiding section is preferably adapted to hold the workpiece in place in the guiding section relative to another workpiece being displaceable in the transfer direction in the delivery location. Therefore only one workpiece may be displaced at a time. In this regard, the guiding section at least adjacent the delivery location is preferably adapted to hold the workpiece in place. This can be achieved, for example, by a mechanical stop (for example formed by the guideway) in the guiding section which is not present in the delivery location.

The delivery location may allow the workpiece to be displaced linearly between the first position and the second position. The delivery location may also be adapted to guide the workpiece for a generally linear displacement between the first position and the second position.

In a preferred embodiment the delivery location has a capacity to hold at least one workpiece. The delivery location may also have a capacity to hold two, three or more workpieces. In this case a set of workpieces in the delivery location is preferably displaceable in a transfer direction relative to the retainer(s) between a first position and a second position. In the first position the retainer(s) engage(s) the workpiece adjacent the retainer(s) and hinder(s) the set of workpieces from being removed from the magazine in the feed direction. In the second position the set of workpieces can bypass the retainer(s) so that removal of the set of workpieces in the feed direction is enabled. In this way, it is possible to remove sets having a predetermined number of workpieces from the magazine. The magazine may also be configured so that the capacity of the delivery location is adjustable. Therefore a user could adjust the number of workpieces contained in a set. The features of the invention described herein for one workpiece apply for a set of workpieces accordingly, as appropriate.

In another embodiment of the invention the retainer(s) is/are adapted to engage with a protrusion(s) of the workpiece in the first position. The retainer(s) in the transfer direction is/are preferably shorter than the length of the workpiece in the same direction. More preferably the retainer(s) in the transfer direction is/are about ½ or ⅓ of the length of the workpiece in the same direction. The device may comprise at least two retainers positioned on opposite sides of the delivery location, or four retainers (two pairs) positioned on opposite sides of the delivery location.

In an embodiment of the invention the device further comprises a workpiece, or a plurality of workpieces. Preferably the workpieces are arranged in a stack, for example in a generally vertical stack with the individual workpieces generally axially aligned with one another, and preferably in a relationship where the workpieces are stacked. The device therefore may comprise a stack of workpieces. Preferably the stack has an end workpiece which is located in the delivery location of the magazine, and at least a second workpiece located in the guiding section of the magazine. For example the stack may comprise two workpieces of which one is located in the delivery location and the other in the guiding section. The magazine may also hold a plurality of workpieces with one or a set of workpieces located in the delivery location, and one or more additional workpieces in the guiding section.

A workpiece as it may be used with the current invention typically comprises a body having a generally H-shaped outer cross-section. The body typically also has major bottom and top planes that are generally parallel to one another. The body preferably has protrusions, preferably formed by the legs of the H-shaped cross-section. However, the protrusions may also be otherwise arranged at the body. For example, the protrusions may be formed by two legs of a generally X shaped cross-section or one or three legs of a generally Y shaped cross-section.

Each of the workpieces preferably has a length in the transfer direction and a protrusion, wherein the protrusion in the transfer direction is shorter than the workpiece in the same direction. The workpiece may also have four protrusions with two pairs of protrusions arranged on opposite sides of the workpiece, and the protrusions of each pair may be spaced from one another. Such a workpiece may, for example, be generally H-shaped having a length along the direction of the middle bar of the H-shape. The protrusions in the direction of the middle bar are shorter than the workpiece in the same direction.

The length of the protrusion(s) in the transfer direction may be ½ or ⅓ of the workpiece length in the same direction, for example. The space between pairs of protrusions, for example as present in the H-shaped workpiece, may be the same as the length of the protrusion(s) in the transfer direction.

In another embodiment of the invention the workpiece in the delivery location may further be displaceable in the transfer direction, and preferably relative to the retainer(s), between the first position and an alternative second position. In the alternative second position the workpiece is preferably enabled to bypass the retainer(s) which preferably allows the workpiece to be removed from the magazine in the feed direction.

A second aspect of the invention is related to a system for handling of workpieces. The system comprises:
    an input buffer comprising a device of the invention,
    an output buffer comprising a device of the invention, and
    an actuator adapted to displace a workpiece of the input buffer from the first position of the input buffer to the second position of the input buffer and simultaneously to displace a workpiece of the output buffer from the second position or the alternative second position of the output buffer to the first position of the output buffer. (A reference to a "second position" in the following also includes the "alternative second position" as an alternative.)

The magazine of the input buffer and the magazine of the output buffer are preferably arranged parallel to one another. The magazines may also be made as one piece, for example, two magazines having a common wall. Preferably the retainer(s) of the input buffer and the retainer(s) of the output buffer are coplanar. The delivery location of the input buffer and the delivery location of the output buffer may also be arranged generally coplanar, and may further have the same capacity for holding workpieces. For example, an input buffer may hold 2 to 20 workpieces which are sequentially machined and then placed in the output buffer.

Preferably the delivery location of the input buffer and the delivery location of the output buffer allow workpieces respectively placed therein to be displaced parallel to one another between their respective first and second positions. Preferably such displacement is in the transfer direction.

A third aspect of the invention is related to a method of handling workpieces by use of a device according to the invention. The method comprises the steps of:
placing a workpiece in the delivery location of the magazine of the device; and
displacing the workpiece between the first and the second position.

The distance between the first position and the second position is preferably less than the length of the workpiece in the transfer direction. Preferably the distance between the first position and the second position is less than 50% of the length of the workpiece in the transfer direction.

Preferably the workpiece in the first position is stacked generally axially aligned with at least one other workpiece in the magazine. The workpiece in the second position is preferably axially offset from another workpiece in the magazine. The workpiece in the delivery location may therefore be axially aligned to the workpiece(s) in the magazine or laterally offset relative to the other workpiece(s) in the magazine.

Preferably the workpiece is placed in the delivery location in the first position and displaced from the first to the second position. The method may further comprise the step of removing the workpiece from the delivery location of the magazine. The method may also further comprise the step of replacing the workpiece removed from the delivery location of the magazine by a workpiece in the guiding section. For example, for removing a workpiece from the magazine the workpiece may be guided into the first position in the delivery location, displaced to the second position and taken out of the delivery location. In a subsequent cycle another workpiece may be guided into the delivery location, displaced, removed, and so on. If the magazine is filled with a stack of workpieces, the workpiece in the second position of delivery location preferably overlaps with an adjacent workpiece of the stack so that both workpieces are in touch with one another but laterally offset. This allows the workpiece being removed from the delivery location to control the movement (preferably downward) of the adjacent workpiece into the delivery location. For example, the workpiece being removed from the delivery location may support the workpiece being guided into the delivery location, and thereby control the speed with which the adjacent workpiece is moved into the delivery location.

Another embodiment of the invention preferably allows replacing a workpiece in the magazine. In this embodiment the workpiece is placed in the delivery location in the second position (for example by moving the workpiece from a location outside the magazine into the delivery location of the magazine in a direction opposite to the feed direction) and displaced from the second to the first position, in which it is retained in the magazine. Preferably the placement of the workpiece in the delivery location moves another workpiece from the delivery location toward the guiding section of the magazine. For example, for restoring a workpiece in the magazine the workpiece may be positioned adjacent the second position of the delivery location moved into the delivery location (in a direction opposite to the feed direction) and displaced laterally to the first position. In a subsequent cycle another workpiece may be positioned, moved into the delivery location, displaced, and so on. If the magazine is filled with workpieces or a stack of workpieces, the workpiece in the delivery location preferably overlaps with the new workpiece to be restored. Thus, the workpiece in the delivery location and the new workpiece are in touch with one another but laterally offset. Therefore moving the new workpiece into the magazine may move other workpiece in the magazine from the delivery location toward the guiding section.

A fourth aspect of the invention is related to a method comprising the steps of
placing a first workpiece in a first device according to the invention, the first device forming an input device;
placing a second workpiece in a second device according to the invention the second device forming an output device; and
simultaneously displacing the first workpiece from the first position of the magazine of the input device to the second position of the magazine of the input device, and displacing the second workpiece from the second position of the magazine of the output device to the first position of the magazine of the output device. Such simultaneous displacement may, for example, allow for using a single actuator for removing a workpiece from the magazine of the input device and restoring another workpiece to the magazine of the output device simultaneously. Therefore an actuator or alternatively process time may be saved. The first and second workpieces may also be placed simultaneously in the magazines of the input device or of the output device, respectively. In a fifth aspect the invention is directed to the use of a workpiece with a device or system of the invention. The workpiece preferably comprises a support frame which is adapted to retain a blank for making a dental restoration. The support frame preferably surrounds the blank and is preferably dimensioned so that the blank does not extend beyond the support frame in any direction. The support frame may have a protrusion, in particular the support frame may have two or three protrusions projecting from circumferential walls of the support frame. The protrusions may, for example, allow for guiding, positioning, and/or clamping the workpiece in a machine for machining dental restorations. The workpiece, or in particular the support frame and/or blank, may comprise an identification code, for example a barcode or a transponder carrying a code. The identification code may be used to track the workpiece in a manufacturing process and/or for maintaining the assignment between the workpiece and a patient who is supposed to receive the dental restoration produced from the workpiece.

In a sixth aspect the invention is related to a machine comprising a device of the invention. Such machine is preferably a milling or grinding machine for making dental restorations.

The present invention may advantageously provide a relatively inexpensive handling device for workpieces. Further the device and method for handling workpieces may allow for a gentle handling of the workpieces. For example, the dental restorations that may be comprised in the workpieces thus may be protected against rough handling, like shocks and collisions, and therefore the yield of the automated process may be increased. The invention may also be implemented by using a relatively small number of parts, which helps to reduce costs on one hand and to increase the reliability and uptime of a machine used with it on the other hand, for example. The invention may also help to reduce handling times in the machine and therefore to increase the machine uptime.

BRIEF DESCRIPTION OF THE DRAWINGS

FIGS. 7a, 7b, 8a, 8b, 9a, 9b are top or bottom views of workpieces having outer shapes according to exemplary embodiments of the invention.

DETAILED DESCRIPTION OF THE DRAWINGS

Figure 1:
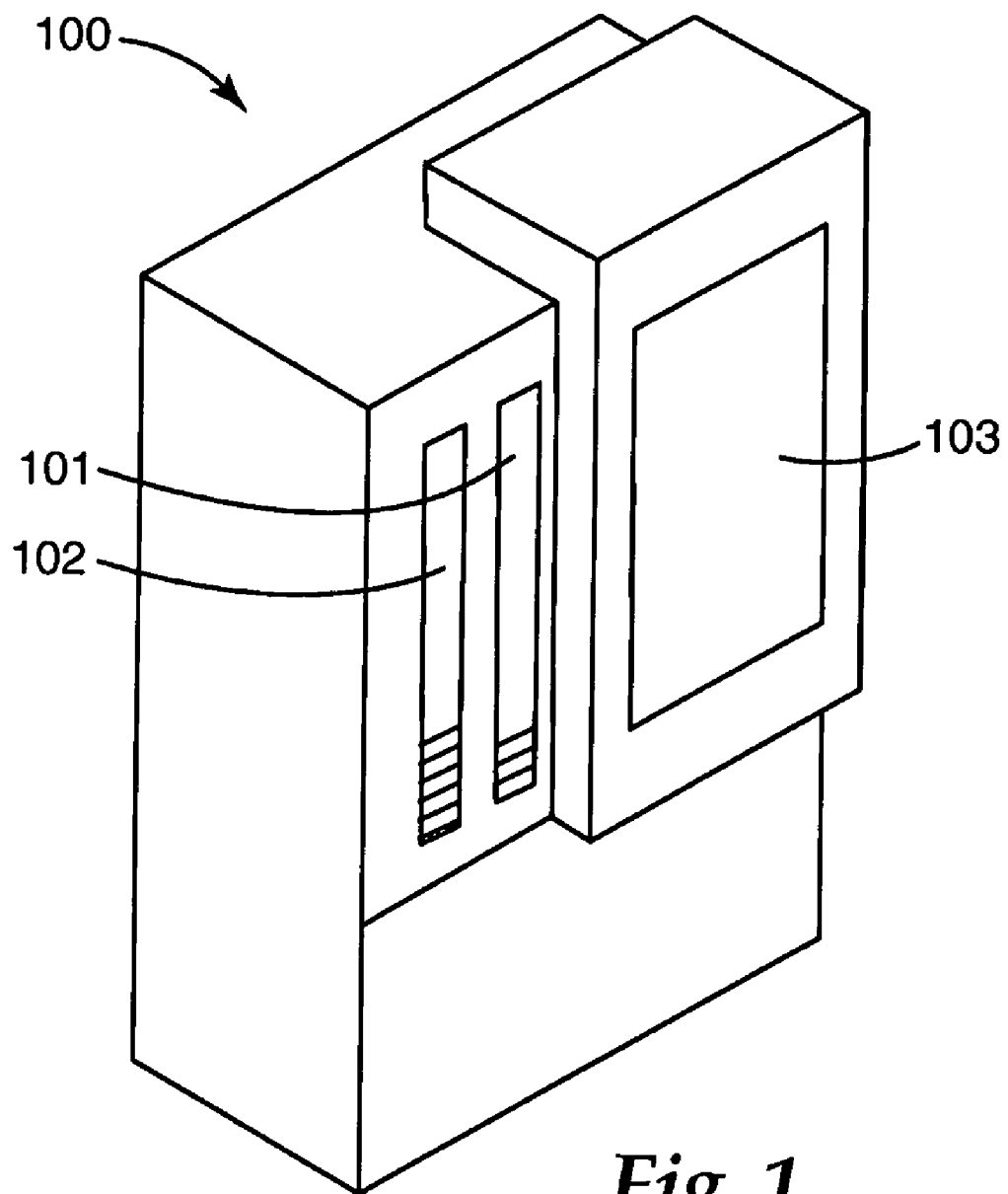
FIG. 1 is a perspective view of a milling machine as it may be used with the present invention.

FIG. 1 shows an example of a machine 100 as it may be used with the present invention. Such machine allows computer-controlled manufacturing of dental ceramic parts, such as copings or bridge frameworks useful in the preparation of dental restorations. A machine for manufacturing dental ceramic parts is, for example, available from 3M ESPE AG, Germany, under the trade designation LAVA™ Milling Unit. The machine 100 is designed to run automatically without the need for constant supervision by an operator. Therefore the machine has an input buffer 101 for holding a plurality of blanks or workpieces which are fed sequentially into a processing area 103 in which they are processed to form the dental restoration components. After the dental parts have been processed to the desired extent they are discharged from the processing area 103 and held in an output buffer 102 that accordingly is made to hold a plurality of finished dental parts. The input and output buffers typically hold enough blanks to permit several hours of continuous processing time without supervision by an operator. Typically the size of the input and the output buffers are substantially equal so that, for example, the machine can process all of the new blanks from the input buffer sequentially and then store them all in the output buffer. Then an operator can replace the filled output buffer with an empty buffer, and replace the empty input buffer with one filled with new blanks, and begin processing the next batch of blanks.

Figure 2:
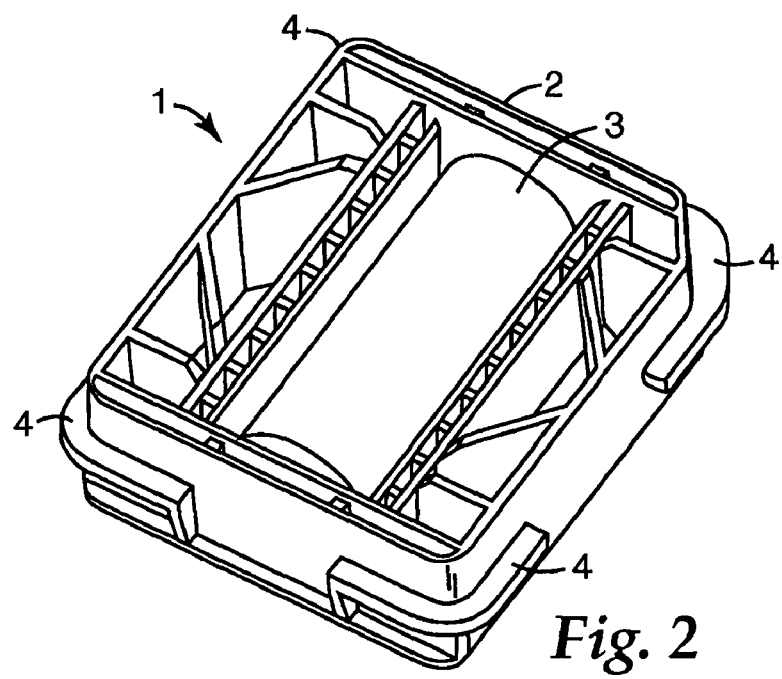
FIG. 2 is a perspective view of a workpiece comprising a dental blank held in a support frame according to an embodiment of the invention.

For handling and protection purposes the blanks and the finished dental restoration components are typically provided in the form of workpieces that usually have a support structure surrounding and holding the blank or dental part. An example of such a workpiece is shown in FIG. 2. In the example shown, the workpiece 1 comprises a support frame 2 and a ceramic blank 3. The support frame 2 surrounds the ceramic blank 3 and holds it in place, preferably by adhesive bond (not shown) between the blank 3 and the support frame 2. The support frame 2 has protrusions 4 by which the support frame 2 may be guided, positioned, and/or clamped, for example, in a machine for machining dental parts. The protrusions could also be part of a slot construction, for example one or more protrusions may be components that form a slot or part of a slot. The protrusions may facilitate the individual removal of a workpiece from a magazine or a stack of workpieces, or the replacement in the magazine or of the workpiece in a stack of workpieces, as will be described below. The support frame is typically made of plastic, and for example, injection molded. Typically the support frame is made of polystyrene (PS), but other possible plastic materials include, for example, polycarbonate (PC), acrylonitrile-butadiene-styrene (ABS), polybutadiene terephthalate (PBT), polymethyl methacrylate (PMMA), polyoxymethylene (POM) or any other suitable polymer.

Figure 3A:
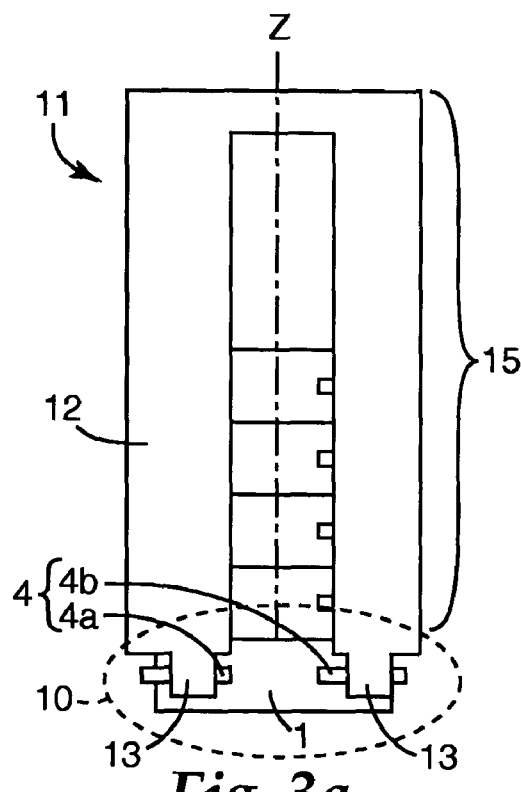
FIG. 3a, 3b are a schematic front and side views of a magazine and workpieces according to an embodiment of the invention.
Figure 3B:
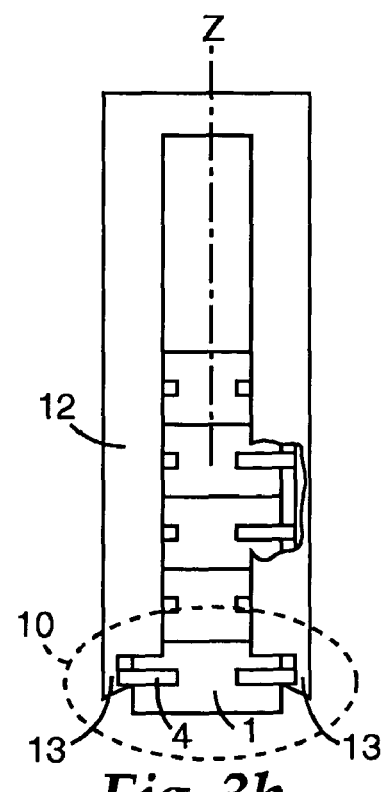

FIGS. 3a and 3b show front and side views of a buffer 11 that holds a plurality of workpieces. The workpieces are stacked on top of each other in a magazine 12 of the buffer 11. The magazine 12 has a guiding section 15 and an adjacent a delivery location 10. The guiding section 15 is configured to guide the workpieces along a feed direction Z by laterally restricting the workpieces in at least on dimension generally transverse to the feed direction Z, and providing for the workpieces remaining generally freely movable along the feed direction Z. The guiding section 15 is thus adapted to guide the workpieces into a first position of the delivery location 10 (shown in FIG. 3a).

In the example shown, the guiding section 15 has generally vertical walls that surround the workpieces, thus preferably restricting the workpieces in all lateral directions. The workpieces therefore may be displaceable laterally only within the inner space or tolerance left between the walls of the magazine 12. Other configurations are however possible, for example, the magazine may be curved or oriented otherwise, for example, at an angle relative to the vertical, or horizontally. Further, the delivery location may alternatively be arranged on the opposite side of the guiding section 15 (in the Figures on top of the guiding section) with an appropriate feed mechanism for moving the workpieces upward. However, the configuration shown has the advantage that workpieces in the magazine automatically move into the delivery location by the aid of gravity. Therefore devices for positioning of the workpieces in the magazine may not be necessary.

In FIG. 3a a workpiece 1 is located in the delivery location 10. The delivery location 10 generally is an area allowing workpieces to be removed from the magazine 12 and/or to be placed into the magazine 12. In contrast to the guiding section, the workpiece when positioned in the delivery location is not restrained in all lateral directions, but displaceable in at least one lateral direction. The delivery location 10 is adapted to co-operate with a workpiece so that the workpiece can pass through if positioned appropriately, but otherwise is retained in the magazine 12. Retainers 13 retain the workpiece in the magazine 12 (FIG. 3b). In the first position of the workpiece 1 (shown in FIG. 3a) the retainers engage the protrusions 4 on opposite sides of the workpiece 1 and thereby retain the workpiece 1 in the magazine 12. Retainers cooperating with slots in a workpiece may also be used instead of retainers cooperating with protrusions in a workpiece. Combinations of protrusions and slots are also possible.

Figure 4A:
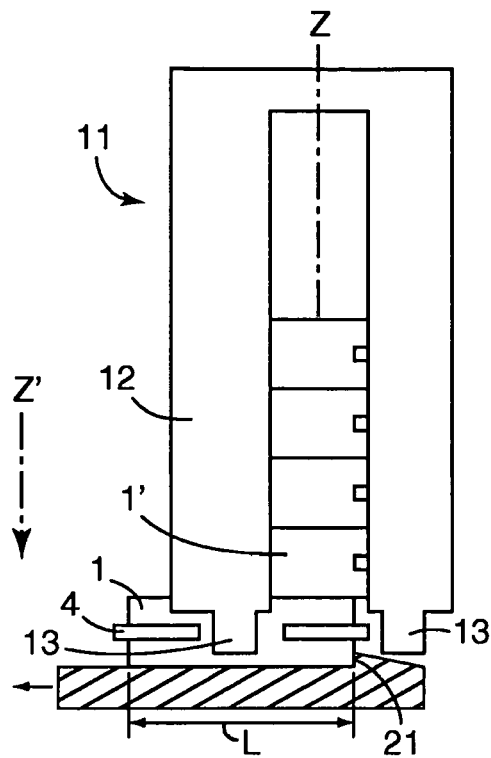
FIGS. 4a, 4b are schematic views illustrating the steps of removing a workpiece from a magazine according to an embodiment of the invention.

FIG. 4a shows the buffer 11 of FIG. 3a, but the workpiece 1 has been displaced laterally from the first position (FIG. 3a) to a second position. In the second position the retainers are disengaged from the protrusions of the workpiece so that the workpiece 1 is free and can be removed in the feed direction Z' away from the magazine. Two of the retainers 13 are disengaged from the protrusions 4 because the retainers 13 are within recesses of the workpiece. In this case the recesses are formed by spaces left between front protrusions 4a and back protrusions 4b of the workpiece.

An actuator 20 is shown which is movable relative to the retainers 13 of the magazine 12. In the example, the actuator 20 is movable generally in and opposite to the feed direction Z' and, when necessary, in a direction generally transverse to the feed direction Z'. However, positioning of the actuator relative to the retainers may, for example, include moving the actuator or the magazine or both relative to each other, as appropriate. The actuator 20 is adapted to displace the workpiece 1 laterally, in the example from the first position (FIG. 3a) to the second position (FIG. 4a). The actuator 20 has a retention member 21 suitable for engaging a surface of the workpiece 1 so that when the actuator is laterally moved (to the left, FIGS. 3a and 4a) to displace the workpiece 1, the retention member 21 restrains the workpiece 1 to prevent it from slipping relative to the actuator 20. At the same time the actuator 20 preferably supports the workpiece 1 so that the workpiece 1 does not fall once it is released from the retainers.

Figure 4B:
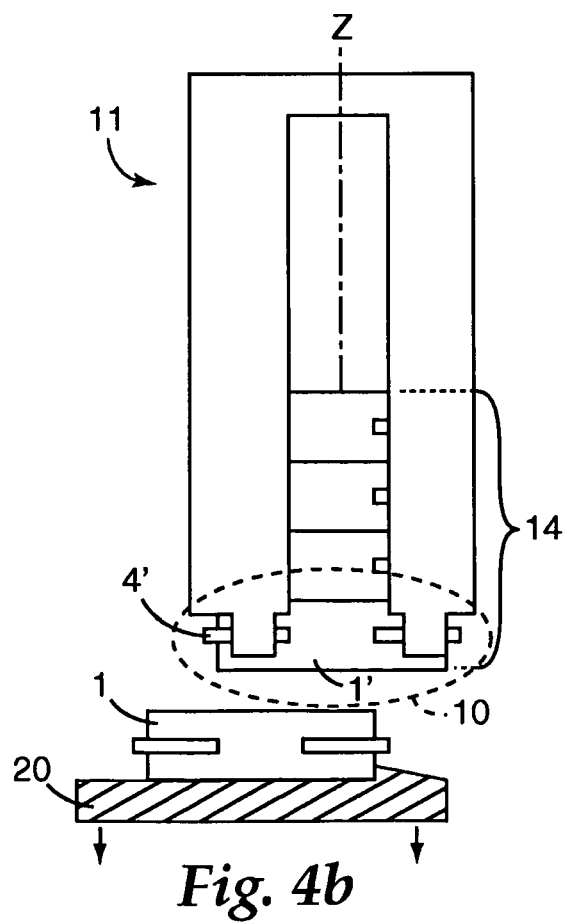

The workpiece 1 in the second position overlaps the adjacent workpiece 1' (FIG. 4a). Therefore the displaced workpiece 1 supports remaining workpieces in the magazine back from falling down and stopping abruptly when they come to rest on the retainers 13. This may be advantageous in case the magazine is substantially vertical with the delivery location arranged towards the bottom of the magazine, or in case the workpiece 1 is positioned in the delivery location by aid of a spring (not shown). The distance between the first position and the second position is therefore preferably shorter than the dimension of the workpieces 1, 1' in the direction of the displacement of workpiece 1. Preferably the workpiece 1 and the adjacent workpiece 1' overlap to an extent that the center of mass of the adjacent workpiece 1' is supported by the workpiece 1 in its second position (FIG. 4a). For example, the workpieces 1, 1' have a length L and the displacement of workpiece 1 is shorter than L, preferably shorter than ½ of L, and most preferably about ⅓ of L. Therefore workpieces supported by a workpiece in the second position are prevented from tilting in the magazine, which could cause jamming of the workpieces in the magazine and result in the suspension of processing of workpieces In FIG. 4b the actuator 20 has been moved downwards relative to FIG. 4a so that the workpiece 1 is displaced from the magazine 12. Thereby the remaining stack 14 of workpieces held in the magazine has been lowered with a new workpiece 1' being placed in the delivery location 10. The speed of the downward movement of the actuator 20 is preferably selected so that the new workpiece 1' smoothly comes to rest on the retainers 13. This is advantageous to prevent any of the workpieces of the stack 14 from being damaged, for example, from cracks caused by mechanical shock, or from tilting in the magazine.

Figure 5A:
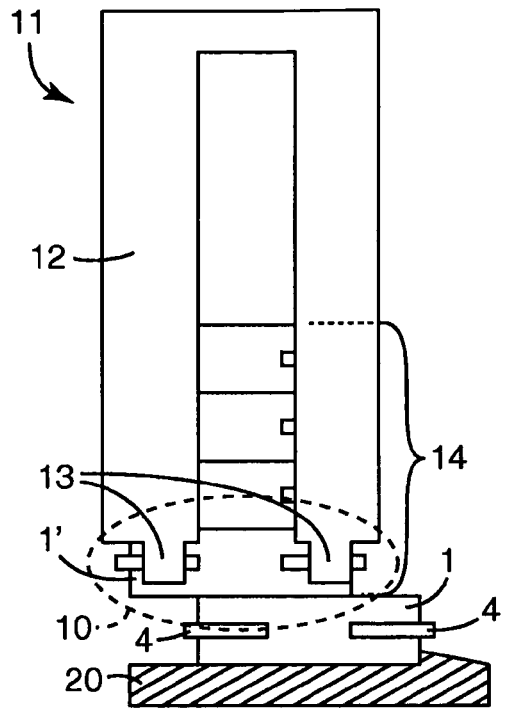
FIGS. 5a-5c are schematic views illustrating the workflow of placing a workpiece into a magazine according to an embodiment of the invention.
Figure 5B:
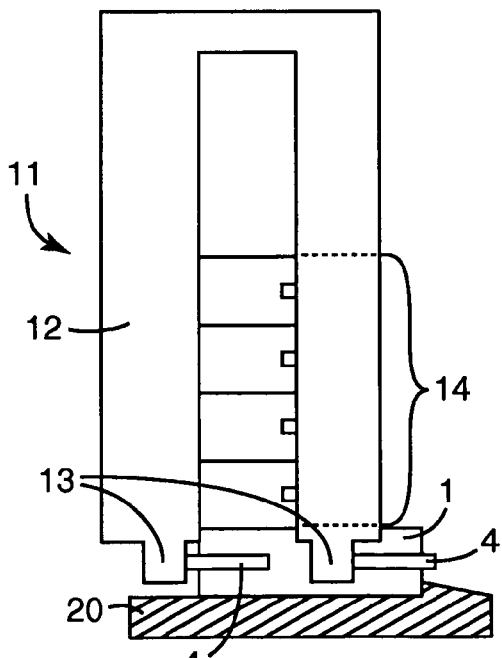
Figure 5C:
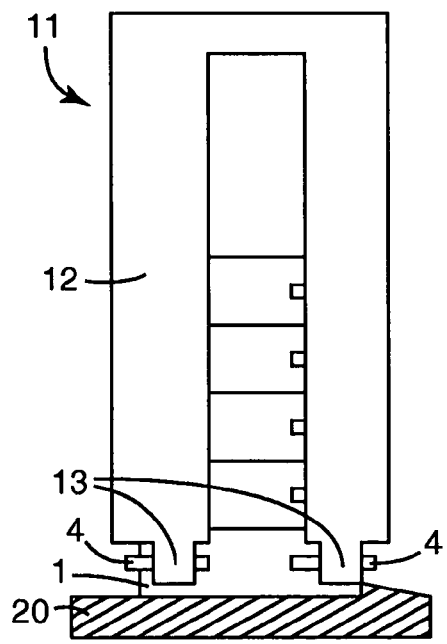

FIGS. 5a, 5b and 5c illustrate the placement of a workpiece 1 into the magazine 12. FIG. 5a shows the workpiece 1 positioned adjacent the last workpiece 1'. The workpiece 1 is laterally offset relative to the workpiece 1' so that the workpieces 1, 1' overlap. The offset of the workpiece 1 is further selected so that the retainers 13 can bypass the protrusions 4 when the workpiece 1 is moved (for example vertically, as shown in FIG. 5b) into the delivery location 10. The workpiece 1 preferably overlaps the balance point of the workpiece 1' as mentioned in the description of FIG. 4a so that the workpiece 1' and others above do not tilt when lifted by the workpiece 1.

The situation with the workpiece 1 moved into the delivery location 10 is shown in FIG. 5b. The workpiece 1 is in a second position in the delivery location in which the protrusions 4 and the retainers 13 are disengaged from one another. The actuator 20 then is moved laterally to displace the workpiece 1 into a first position in the delivery location as is shown in FIG. 5c. The second position shown in FIG. 5b (offset to the right) is an alternative position of the second position shown in FIG. 4a (offset to the left). The second position shown in FIG. 5b corresponds to the second "alternative second position" as described above. Therefore restoring a workpiece to the magazine 12 may also be done with the workpiece initially being positioned in the second position as shown in FIG. 4a, or in the alternative second position as shown in FIG. 5b.

Figure 6A:
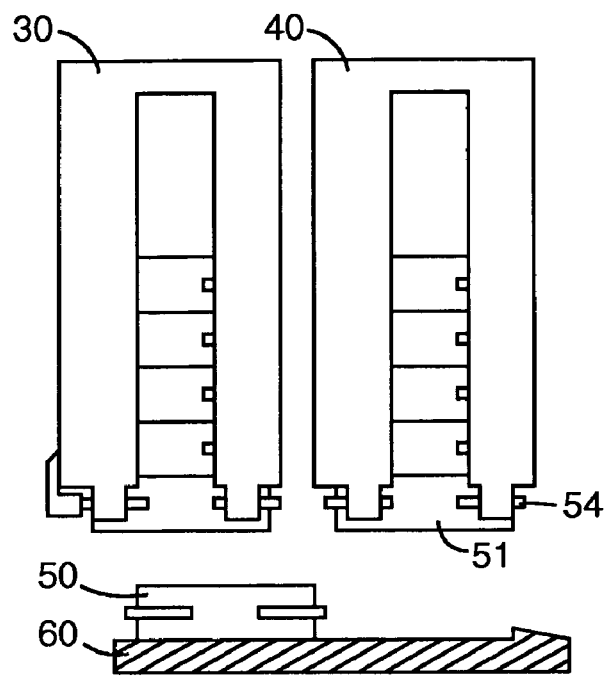
FIGS. 6a-6d are schematic views illustrating the workflow of placing a first workpiece into a first magazine and removing a second workpiece from a second magazine according to an embodiment of the invention.

FIGS. 6a, 6b, 6c and 6d illustrate the process of removing a workpiece 51 from an input buffer 40 and restoring another workpiece 50 to an output buffer 30. In FIG. 6a an actuator 60 carries the workpiece 50 that, for example, was picked up from a processing area in which the blank held in the workpiece 50 was processed, for example, machined.

Figure 6B:
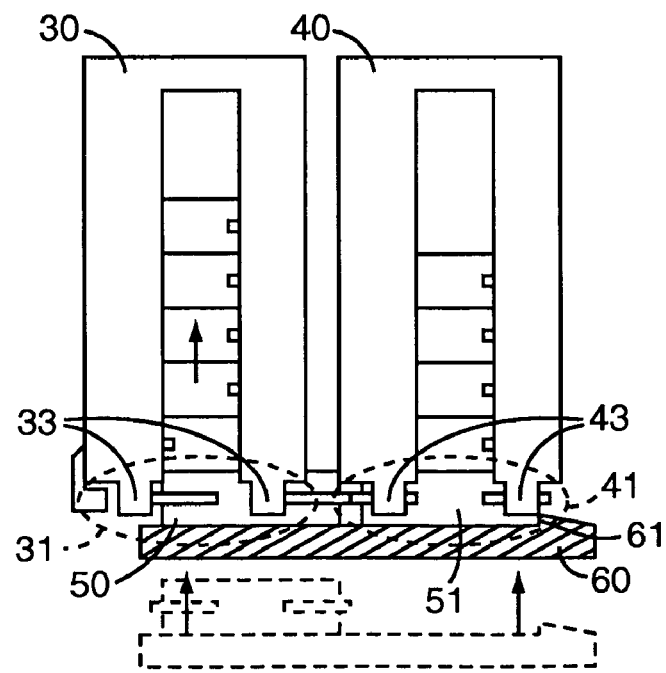

FIG. 6b relative to FIG. 6a shows the actuator positioned further upward and the workpiece 50 moved into the delivery location 31 of the output buffer 30. Other workpieces that are eventually present in the output buffer 30 (as shown) thereby are lifted by the workpiece 50 when it enters the delivery location 31. In the position shown in FIG. 6b the workpiece 50 is disengaged from the retainers 33 and in a second position in the delivery location 31. On the other hand, the workpiece 51 is in a first position in the delivery location 41, meaning that the workpiece 51 is engaged with the retainers 43 of the input buffer 40.

Figure 6C:
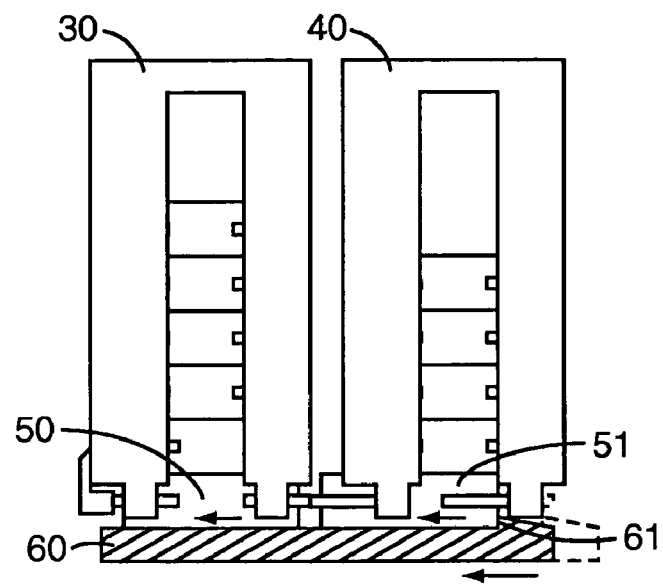

In FIG. 6c the actuator 60 is shown in a position after a sideward movement (a movement to the left, in the Figure). The actuator, using a retention member 61, has displaced the workpiece 51 from its first position (FIG. 6b) to a second position (FIG. 6c) in the delivery location 41. Simultaneously the workpiece 50 of the output buffer 30 has been displaced from an (alternative) second position to a first position. In the example shown the workpiece 51 of the input buffer and the workpiece 50 of the output buffer are located adjacent to one another so that a displacement of the former causes a displacement of the latter. Therefore, a displacement of the workpiece 51 from the first position into the second position in the delivery location 41 causes the workpiece 50 to be displaced from the second position into the first position of the in the delivery location 31. Alternatively, the workpieces of the input and output buffers could each be displaced by the actuator, meaning that the two workpieces do not necessarily have to be located adjacent to one another so that one displaces the other. For example, the actuator may have two retention members for engaging and displacing of each of the two workpieces.

Figure 6D:
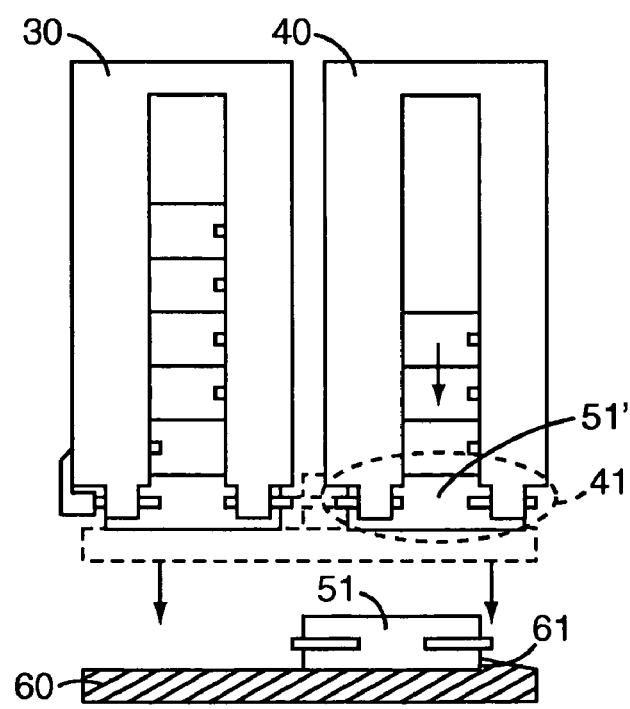

FIG. 6d shows the actuator being positioned downwards (further away form the input and output buffers). Workpieces that, as indicated, eventually are present in the input buffer 40 have moved further down so that a new workpiece 51' is located in the delivery location 41, thus being made available for removal from the delivery location 41 in a subsequent handling cycle. The workpiece 51 carried by the actuator can, for example, now be placed into a processing area where the blank held in workpiece 51 may be processed. The processed workpiece 51 may afterwards be picked up again from the processing area by the actuator 60. However, the workpiece 51 would then be preferably placed at a position on the actuator that corresponds to the position indicated in FIG. 6*a*. FIGS. 7*a*, 7*b*, 8*a*, 8*b*, 9*a*, 9*b* show different shapes of workpieces as they may be used with the current invention. In FIGS. 7*a* and 7*b* a generally H-shaped workpiece 1 is shown as described in detail above. The workpiece 1 has protrusions 4. In FIG. 7*a* the workpiece 1 is shown in the first position in which it is engaged by retainers 13. In particular, the retainers 13 engage the protrusions 4 of the workpiece 1, and in FIG. 7*b* where the workpiece is shown in the second position two of the retainers 13 are within recesses of the workpieces, or in other words the retainers are disengaged from the protrusions 13. In FIGS. 8*a*, 8*b* a workpiece 100 is shown. The workpiece 100 is engaged by retainers 113. The workpiece 100 may be formed and oriented to provide structures 104 that correspond to protrusions according to the invention. In this case two edges of a rectangular shape correspond to the protrusions. The structures 104 or protrusions are engaged by the retainers 113 when the workpiece is in the first position (FIG. 8*a*) and disengaged from the retainers 113 when the workpiece is in the second position (FIG. 8*b*). In FIGS. 9*a*, 9*b* a workpiece 200 is shown which by segments of the circular workpiece serving as protrusions 204 cooperates with retainers 213. FIG. 9*a* shows the workpiece in the first position, and FIG. 9*b* shows the workpiece in the second position.

Other configurations of a workpiece may be possible, for example workpieces having a shape combining any of the shapes mentioned above, or any other suitable shape.

The skilled person will appreciate that the present invention may also be used for other manufacturing machines, like grinding or rapid prototyping machines for making dental parts.

The invention claimed is:

1. A device for handling workpieces, the device comprising:
    a magazine for holding at least one workpiece,
    the magazine having a guiding section for guiding a workpiece in a feed direction toward a delivery location of the magazine in which the workpiece is displaceable in a transfer direction between a first position and a second position,
    the magazine comprising at least one retainer at the delivery location,
    wherein in the first position the retainer(s) engage(s) the workpiece and restrains the workpiece in the feed direction, and
    in the second position the workpiece is enabled to bypass the retainer(s) in the feed direction, wherein the device further comprises four retainers with two pairs positioned on opposite sides of the delivery location.

2. The device of claim 1, wherein the transfer direction is substantially transverse to the feed direction.

3. The device claim 1, wherein the distance between the first position and the second position is less than the length of the workpiece in the transfer direction.

4. The device of claim 1, wherein the distance between the first position and the second position is less than 50% of the length of the workpiece in the transfer direction.

5. The device of claim 1, wherein in the guiding section the workpiece is movable in the feed direction, but displacement of the workpiece in the transfer direction is restricted.

6. The device of claim 5, wherein the guiding section is adapted to guide the workpiece into the delivery location in the first position.

7. The device of claim 1, wherein the guiding section is adapted to restrict displacement of the workpiece in other directions transverse to the feed direction.

8. The device of claim 1, wherein the guiding section is adapted to hold a workpiece in place in the guiding section relative to another workpiece in the delivery location that is displaceable in the transfer direction.

9. The device of claim 1, wherein the retainer(s) is/are adapted to engage with (a) protrusion(s) of the workpiece in the first position.

10. The device of claim 1, wherein the retainer(s) in the transfer direction is/are shorter than the length of the workpiece in the same direction.

11. The device of claim 10, wherein the retainers in the transfer direction is/are about ⅓ of the length of the workpiece in the same direction.

12. The device of claim 1, comprising at least two retainers positioned on opposite sides of the delivery location.

13. The device of claim 1, comprising a workpiece.

14. The device of claim 13, wherein the workpiece has a length in the transfer direction and a protrusion, wherein the protrusion in the transfer direction is shorter than length of the workpiece in the same direction.

15. The device of claim 14, wherein the workpiece has four protrusions with two pairs of protrusions arranged on opposite sides of the workpiece, and the protrusions of each pair are spaced from one another.

16. The device of claim 1, comprising a stack of workpieces.

17. The device of claim 1, wherein in the delivery location the workpiece is further displaceable in the transfer direction between the first position and an alternative second position, wherein in the alternative second position the workpiece is enabled to bypass the retainer(s) which allows the workpiece to be removed from the magazine in the feed direction.

18. A system for handling of workpieces comprising:
    an input buffer comprising a device of claim 1,
    an output buffer comprising a device of claim 1, and
    an actuator adapted to displace a workpiece of the input buffer from the first position of the input buffer to the second position of the input buffer and simultaneously to displace a workpiece of the output buffer from the (alternative) second position of the output buffer to the first position of the output buffer.

19. The system of claim 18, wherein the magazine of the input buffer and the magazine of the output buffer are arranged parallel to one another.

20. The system of claim 18, wherein the retainer(s) of the input buffer and the retainer(s) of the output buffer are arranged within a generally common plane.

21. The system of claim 18, wherein the delivery location of the input buffer and the delivery location of the output buffer allow workpieces respectively placed therein to be displaced parallel to one another between their respective first and second positions.

22. A method of handling workpieces by use of a device according to claim 1, comprising the steps of:
    placing a workpiece in the delivery location of the magazine of the device; and
    displacing the workpiece between the first and the second position.

23. The method of claim 22, wherein the workpiece is displaced between the first position and the second position by less than the length of the workpiece in the transfer direction.

24. The method of claim 23, wherein the workpiece is displaced between the first position and the second position by less than 50% of the length of the workpiece in the transfer direction.

25. The method of claim 22, wherein the workpiece in the first position is generally axially aligned with at least one other workpiece in the magazine.

26. The method of claim 22, wherein the workpiece in the second position is axially offset from another workpiece in the magazine.

27. The method of claim 22, wherein the workpiece is placed in the delivery location in the first position and displaced from the first to the second position.

28. The method of claim 27, further comprising the step of removing the workpiece from the delivery location of the magazine.

29. The method of claim 28, further comprising the step of replacing the workpiece removed from the delivery location of the magazine by a workpiece in the guiding section.

30. The method of claim 22, wherein the workpiece is placed in the delivery location in the second position and displaced from the second to the first position.

31. The method of claim 30, wherein the placement of the workpiece in the delivery location moves another workpiece from the delivery location toward the guiding section of the magazine.

32. A method of handling workpieces, comprising the steps of:
placing a first workpiece in a first device according to claim 1, the first device forming an input device;
placing a second workpiece in a second device according to claim 1, the second device forming an output device; and
simultaneously displacing the first workpiece from the first position of the magazine of the input device to the second position of the magazine of the input device, and displacing the second workpiece from the second position of the magazine of the output device to the first position of the magazine of the output device.

33. A use of a workpiece with a device according to claim 1, wherein the workpiece comprises a support frame adapted to retain a blank for making a dental restoration, wherein the support frame surrounds the blank and is dimensioned so that the blank does not extend beyond the support frame in any direction.

34. The use of a workpiece of claim 33, wherein the workpiece comprises an identification code.

35. A machine, comprising a device according to claim 1.

* * * * *

UNITED STATES PATENT AND TRADEMARK OFFICE
CERTIFICATE OF CORRECTION

PATENT NO. : 8,251,254 B2
APPLICATION NO. : 12/671521
DATED : August 28, 2012
INVENTOR(S) : Sebastian Guggenmos Page 1 of 1

It is certified that error appears in the above-identified patent and that said Letters Patent is hereby corrected as shown below:

First Page Column 1 (Assignee)
Line 1                  Delete "Innovatives" and insert -- Innovative --, therefor.

Column 6
Line 23                 Delete "steps of" and insert -- steps of: --, therefor.

Column 9
Line 52                 Delete "workpieces" and insert -- workpieces. --, therefor.

Column 10
Line 62                 Delete "form" and insert -- from --, therefor.

Signed and Sealed this
Thirteenth Day of November, 2012

David J. Kappos
*Director of the United States Patent and Trademark Office*